United States Patent
Yoshida et al.

(10) Patent No.: US 10,232,358 B2
(45) Date of Patent: Mar. 19, 2019

(54) PENTASIL-TYPE ZEOLITE, AND METHOD FOR MANUFACTURING SAME

(71) Applicant: TOSOH CORPORATION, Yamaguchi (JP)

(72) Inventors: Satoshi Yoshida, Yamaguchi (JP); Yukio Ito, Yamaguchi (JP); Hidenori Yamada, Yamaguchi (JP)

(73) Assignee: TOSOH CORPORATION, Yamaguchi (JP)

(*) Notice: Subject to any disclaimer, the term of this patent is extended or adjusted under 35 U.S.C. 154(b) by 0 days.

(21) Appl. No.: 14/913,093

(22) PCT Filed: Aug. 12, 2014

(86) PCT No.: PCT/JP2014/004177
§ 371 (c)(1),
(2) Date: Feb. 19, 2016

(87) PCT Pub. No.: WO2015/029355
PCT Pub. Date: Mar. 5, 2015

(65) Prior Publication Data
US 2016/0199824 A1    Jul. 14, 2016

(30) Foreign Application Priority Data
Aug. 30, 2013 (JP) ................. 2013-178999

(51) Int. Cl.
*B01J 29/85* (2006.01)
*B01J 35/10* (2006.01)
(Continued)

(52) U.S. Cl.
CPC .............. *B01J 29/40* (2013.01); *B01J 29/85* (2013.01); *B01J 35/002* (2013.01);
(Continued)

(58) Field of Classification Search
None
See application file for complete search history.

(56) References Cited

U.S. PATENT DOCUMENTS 6,180,550 B1    1/2001  Beck et al.
2015/0321185 A1*  11/2015 Ueno ................ B01J 37/0246
                                                                502/66

FOREIGN PATENT DOCUMENTS

JP      60-251121    12/1985
JP      7-308581     11/1995
(Continued)

OTHER PUBLICATIONS

JP2006334454A_English Translation.*
(Continued)

*Primary Examiner* — Colin W. Slifka
(74) *Attorney, Agent, or Firm* — Greenblum & Bernstein, P.L.C.

(57) ABSTRACT

[Problem] The purpose of the present invention is to provide: a pentasil-type zeolite that combines a higher BET specific surface area and a higher acid amount than previously; and a method for manufacturing said pentasil-type zeolite.
[Solution] A pentasil-type zeolite characterized in that the BET specific surface area thereof is 450 $m^2/g$ or more, and furthermore the acid amount thereof, measured by the ammonia-TPD method, is 0.38 mmol/g or more. This pentasil-type zeolite can be obtained by a manufacturing method which has a crystallization step for crystallizing a mixture containing tetrabutylphosphonium cations, a silica source, an alumina source, an alkali metal source, and water, and which is characterized in that the molar ratio of the alkali metal relative to the silica in the mixture is greater than 0.04 and less than 0.10.

14 Claims, 3 Drawing Sheets

(51) Int. Cl.
| | |
|---|---|
| *B01J 37/04* | (2006.01) |
| *C01B 39/54* | (2006.01) |
| *C07C 4/18* | (2006.01) |
| *C07C 5/13* | (2006.01) |
| *B01J 29/40* | (2006.01) |
| *C07C 1/24* | (2006.01) |
| *C07C 1/20* | (2006.01) |
| *C07C 6/12* | (2006.01) |
| *B01J 35/00* | (2006.01) |
| *B01J 35/02* | (2006.01) |
| *C01B 39/40* | (2006.01) |

(52) U.S. Cl.
CPC ......... *B01J 35/0013* (2013.01); *B01J 35/023* (2013.01); *B01J 35/1019* (2013.01); *B01J 35/1038* (2013.01); *B01J 35/1042* (2013.01); *B01J 35/1057* (2013.01); *B01J 35/1061* (2013.01); *B01J 37/04* (2013.01); *C01B 39/40* (2013.01); *C01B 39/54* (2013.01); *C07C 1/20* (2013.01); *C07C 1/24* (2013.01); *C07C 4/18* (2013.01); *C07C 5/13* (2013.01); *C07C 6/123* (2013.01); *C01P 2006/12* (2013.01); *C01P 2006/14* (2013.01); *C07C 2529/40* (2013.01); *Y02P 20/52* (2015.11)

(56) References Cited

FOREIGN PATENT DOCUMENTS

| | | | | |
|---|---|---|---|---|
| JP | 2002-535222 | 10/2002 | | |
| JP | 2006-334454 | 12/2006 | | |
| JP | 2006334454 A | * | 12/2006 | ............... B01J 20/18 |

OTHER PUBLICATIONS

Extended European Search Report issued in Patent Application No. 1480601.0, dated Mar. 24, 2017.
Minkee Choi et al., "Stable single-unit-cell nanosheets of zeolite MFI as active and long-lived catalysts", Nature, Sep. 10, 2009, pp. 246-249, vol. 461.
Xueyi Zhang et al., "Synthesis of Self-Pillared Zeolite Nanosheets by Repetitive Branching", Science, 2012, pp. 1684-1687, vol. 336.
International Search Report issued in PCT/JP2014/004177, dated Nov. 18, 2014.
International Preliminary Examination Report in PCT/JP2014/004177 dated Mar. 10, 2016.

* cited by examiner

PENTASIL-TYPE ZEOLITE, AND METHOD FOR MANUFACTURING SAME

TECHNICAL FIELD

The present invention relates to a pentasil-type zeolite, and in particular, to a pentasil-type zeolite having a high catalytic activity.

BACKGROUND ART

A pentasil-type zeolite having a higher BET specific surface area has been investigated since a high activity, a high yield, and a long lifetime of the pentasil-type zeolite as a catalyst as well as high adsorption of the pentasil-type zeolite as an adsorbent or high ion exchange rate of the pentasil-type zeolite as an ion exchanger can be expected. As the pentasil-type zeolite having a higher BET specific surface area, a microcrystalline pentasil-type zeolite and a thin-layered pentasil-type zeolite have been investigated.

As the microcrystalline pentasil-type zeolite, ZSM-5 that is obtained from a starting mixture having a $SiO_2/Al_2O_3$ molar ratio of 350 and has a BET specific surface area of 412.5 $m^2/g$ and an acid amount measured by an ammonia-TPD method of 0.24 mmol/g has been reported (Patent Literature 1). Patent Literature 2 reports a microcrystalline pentasil-type zeolite having a $SiO_2/Al_2O_3$ molar ratio of 15 and a BET specific surface area of 415 $m^2/g$.

On the other hand, as the thin-layered pentasil-type zeolite, an MFI type zeolite composed of a multilamellar structure that is synthesized using an organic surfactant having two ammonium functional groups and has a $SiO_2/Al_2O_3$ molar ratio of 96, a BET specific surface area of 520 $m^2/g$, and a solid acid amount measured by an ammonia-TPD method of 0.31 mmol/g has been reported (Non-Patent Literature 1).

Non-Patent Literature 1 also reports an MFI type zeolite composed of a unilamellar structure having a $SiO_2/Al_2O_3$ molar ratio of 106, a BET specific surface area of 710 $m^2/g$, and a solid acid amount measured by an ammonia-TPD method of 0.33 mmol/g.

A thin-layered pentasil-type zeolite that is obtained from a starting mixture containing tetrabutylphosphonium hydroxide and has a $SiO_2/Al_2O_3$ molar ratio of 150 or more has been disclosed (Non-Patent Literature 2). The pentasil-type zeolite has a form having a repetitive structure in which a thin-layered pentasil-type zeolite having a thickness of about 2 nm extends linearly.

CITATION LIST

Patent Literature

Patent Literature 1: JPS60-251121
Patent Literature 2: JP2002-535222

Non-Patent Literature

Non-Patent Literature 1: Nature, Vol. 461, p. 246 (2009)
Non-Patent Literature 2: Science, Vol. 336, p. 1684 (2012)

SUMMARY OF INVENTION

Technical Problem

Both the pentasil-type zeolites of Patent Literatures 1 and 2 are finely granulated, that is, the particle diameters thereof are three-dimensionally decreased to increase the BET specific surface areas thereof. However, the three-dimensional granulation causes the particles to be unstable, e.g., tightly aggregate. Therefore, it is difficult that the zeolites have a BET specific surface area of 420 $m^2/g$ or more. In contrast, the thin-layered pentasil-type zeolite has a higher BET specific surface area than that of the microcrystalline pentasil-type zeolite. The pentasil-type zeolite of Non-Patent Literature 1 has a high BET specific surface area and an appropriate $SiO_2/Al_2O_3$ molar ratio but a lower acid amount. The pentasil-type zeolite of Non-Patent Literature 2 has a high $SiO_2/Al_2O_3$ molar ratio, and therefore the acid amount is low. In addition, in the manufacture method of Non-Patent Literature 2, a pentasil-type zeolite having a low $SiO_2/Al_2O_3$ molar ratio cannot be obtained.

It is an object of the present invention to provide a pentasil-type zeolite having a higher BET specific surface area and a higher acid amount than those of conventional ones. It is also an object to provide a method for manufacturing the same.

Solution to Problem

In the present invention, a pentasil-type zeolite having a higher BET specific surface area and a higher acid amount than those of conventional one has been investigated. As a result, it has been found that when a structure directing agent that is cheaper than a structure directing agent for obtaining a conventional thin-layered pentasil-type zeolite is used and a raw material mixture having a specific composition is crystallized, a thin-layered pentasil-type zeolite having a high acid amount can be obtained. In addition, it has been found that such a thin-layered pentasil-type zeolite can serve as a catalyst for manufacturing an aromatic hydrocarbon, which is more excellent than the conventional pentasil-type zeolite.

Specifically, the essential points of the present invention are as follows:

[1] A pentasil-type zeolite having a BET specific surface area of 450 $m^2/g$ or more and an acid amount measured by an ammonia-TPD method of 0.38 mmol/g or more.

[2] The pentasil-type zeolite according to the above-described [1], wherein the pentasil-type zeolite has a pore volume being 0.60 mL/g or less.

[3] The pentasil-type zeolite according to the above-described [1] or [2], wherein the pentasil-type zeolite has a molar ratio being silica to alumina of less than 150.

[4] The pentasil-type zeolite according to any one of the above-described [1] to [3], wherein the pentasil-type zeolite has a molar ratio of tetra-coordinated aluminum to the sum of the tetra-coordinated aluminum and hexa-coordinated aluminum in a crystal being 90% or more.

[5] The pentasil-type zeolite according to any one of the above-described [1] to [4], wherein the pentasil-type zeolite contains an alkali metal, with a molar ratio of the alkali metal to aluminum being 0.5 or less.

[6] The pentasil-type zeolite according to any one of the above-described [1] to [5], wherein primary particles do not regularly aggregate.

[7] The pentasil-type zeolite according to any one of the above-described [1] to [6], wherein secondary particles has a diameter of aggregate of 0.3 to 50 μm.

[8] The pentasil-type zeolite according to any one of the above-described [1] to [7], wherein the pentasil-type zeolite contains phosphorus.

[9] The pentasil-type zeolite according to the above-described [8], wherein the pentasil-type zeolite has a molar ratio of phosphorus to silicon and aluminum being 0.0005 or more.
[10] The pentasil-type zeolite according to any one of the above-described [1] to [9], wherein the acid amount measured by an ammonia-TPD method is 0.45 mmol/g or more.
[11] A method for manufacturing the pentasil-type zeolite according to any one of the above-described [1] to [10], the method including a crystallisation step of crystallising a mixture containing tetrabutylphosphonium cations, a silica source, an alumina source, an alkali metal source, and water, wherein a molar ratio of the alkali metal source to silica in the mixture is more than 0.04 and less than 0.10.
[12] The manufacturing method according to the above-described [11] wherein a molar ratio of tetrabutylsulfonium cations to silica in the mixture is 0.04 or more and 0.3 or less.
[13] The manufacturing method according to the above-described [11] or [12], wherein the mixture has the following molar composition:
$SiO_2/Al_2O_3$ of 40 or more and 200 or less,
$TBP/SiO_2$ of 0.04 or more and 0.3 or less,
$SO_4/SiO_2$ of 0 or more and 0.1 or less,
$OH/SiO_2$ of 0.05 or more and 0.5 or less,
$H_2O/SiO_2$ of 5 or more and 40 or less, and
$M/SiO_2$ of more than 0.04 and less than 0.1
(TBP represents tetrabutylphosphonium cations, and M represents the alkali metal).
[14] A catalyst containing the pentasil-type zeolite according to any one of the above-described [1] to [10].
[15] A method for manufacturing an aromatic hydrocarbon using a catalyst containing the pentasil-type zeolite according to anyone of the above-described [1] to [10].

Advantageous Effects of Invention

The present invention can provide a pentasil-type zeolite having a higher BET specific surface area and a higher acid amount than those of conventional ones, and a method for manufacturing the same.

DESCRIPTION OF EMBODIMENTS

Figure 1:
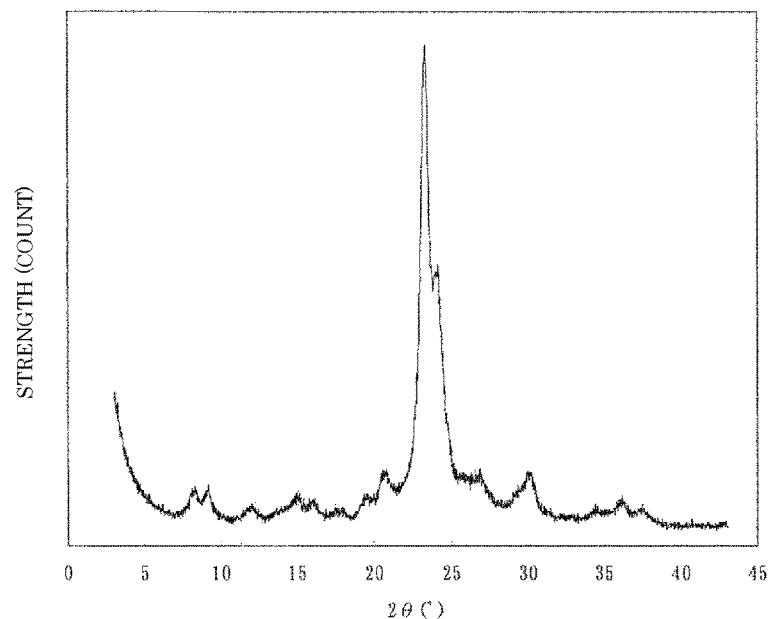
FIG. 1 is a powder X-ray diffraction diagram of a crystallized pentasil-type zeolite obtained in Example 1.

Hereinafter, a pentasil-type zeolite of this embodiment will be described.
This embodiment relates to a pentasil-type zeolite. The pentasil-type zeolite is a zeolite containing a combination of oxygen-containing five-membered rings. The pentasil-type zeolite may be at least one selected from the group consisting of MFI and MEL, which stand for Framework Type Codes defined by International Zeolite Association (hereinafter referred to as "IZA"), and intergrown crystal structures thereof. Specifically, the pentasil-type zeolite may be at least one selected from the group consisting of ZSM-5, silicalite-1, ZSM-11, silicalite-2, and intergrown crystal structures thereof. The pentasil-type zeolite of this embodiment is a pentasil-type aluminosilicate, and examples of the preferred pentasil-type zeolite may include at least one of ZSM-5 and a intergrown crystal structure containing ZSM-5, and particularly ZSM-5.

A crystalline phase of the pentasil-type zeolite can be identified by comparison with at least one of a powder X-ray diffraction (hereinafter referred to as "XRD") pattern described in Collection of simulated XRD powder patterns for zeolites, Fifth revised edition, p. 483 (2007) and an XRD pattern described in The Pentasil Family of Disorder in Zeolite Frameworks in the homepage (http://www.iza-struture.org/databases/) of The Structure Commission of IZA.

The BET specific surface area (BET) of the pentasil-type zeolite of this embodiment is 450 $m^2/g$ or more, preferably 500 $m^2/g$ or more, and more preferably 510 $m^2/g$ or more (BET≥450 $m^2/g$, preferably BET≥500 $m^2/g$, and more preferably BET≥510 $m^2/g$). When the pentasil-type zeolite of this embodiment has the acid amount to be described later and a BET specific surface area of 450 $m^2/g$ or more, the pentasil-type zeolite serves as a catalyst having a high catalytic activity, a high aromatic hydrocarbon selectivity, and a high coking resistance. It is preferable that the BET specific surface area is higher. The BET specific surface area of the pentasil-type zeolite of this embodiment is usually 800 $m^2/g$ or less (BET≤800 $m^2/g$), particularly 700 $m^2/g$ or less (BET≤700 $m^2/g$), and further particularly 600 $m^2/g$ or less (BET≤600 $m^2/g$).

In this embodiment, the BET specific surface area can be measured by a measurement method in accordance with JIS8830 (method for measuring the specific surface area of powders (solids) by gas adsorption). In the measurement, the BET specific surface area can be determined using nitrogen as an adsorption gas by a single point method (relative pressure: p/p0=0.30).

The acid amount measured by an ammonia-TPD method (a, hereinafter sometimes simply referred to as "acid amount") of the pentasil-type zeolite of this embodiment is 0.38 mmol/g or more, preferably 0.40 mmol/g or more, more preferably 0.42 mmol/g or more, further preferably 0.45 mmol/g or more, and still more preferably 0.50 mmol/g or more (a≥0.38 mmol/g, preferably a≥0.40 mmol/g, more preferably a≥0.42 mmol/g, further preferably a≥0.45 mmol/g, and still more preferably a≥0.50 mmol/g). When the pentasil-type zeolite of this embodiment has the above-described BET specific surface area and the acid amount falling within this range, the pentasil-type zeolite has a high catalytic activity, in particular, a high aromatic hydrocarbon selectivity. As the acid amount is higher, the aromatic hydrocarbon selectivity tends to be higher. Specifically, the acid amount of the pentasil-type zeolite of this embodiment is 1.0 mmol/g or less (a≤1.0 mmol/g), and particularly 0.60 mmol/g or less (a≤0.60 mmol/g).

It is preferable that the pentasil-type zeolite of this embodiment have a BET specific surface area of 500 $m^2/g$ or more and 600 $m^2/g$ or less and an acid amount of 0.40 mmol/g or more and 0.60 mmol/g or less (500 $m^2/g$≤BET≤600 $m^2/g$ and 0.40 mmol/g≤a≤0.60 mmol/g), more preferably a BET specific surface area of 500 $m^2/g$ or more and 600 $m^2/g$ or less and an acid amount of 0.45 mmol/g or more and 0.60 mmol/g or less (500 m²/g≤BET≤600 m²/g and 0.45 mmol/g≤a≤0.60 mmol/g), and further preferably a BET specific surface area of 510 m²/g or more and 600 m²/g or less and an acid amount of 0.50 mmol/g or more and 0.60 mmol/g or less (510 m²/g≤BET≤600 m²/g and 0.50 mmol/g≤5≤a≤0.60 mmol/g).

In this embodiment, the acid amount is a value measured by an ammonia-TPD method in accordance with "Measurement of Acidic Properties of Zeolites using Temperature-Programmed Desorption of Ammonia, Catalyst, vol. 42, p. 218 (2000)." It is preferable that the acid amount in this embodiment be a value obtained by measurement of an amount of ammonia that is desorbed at 100 to 700° C. from a pentasil-type zeolite that is obtained by saturation with ammonia and adsorption of ammonia at room temperature. Specifically, a sample is saturated with ammonia at room temperature to allow ammonia to be adsorbed to the sample, and the sample is heated to 100° C. to remove ammonia remaining in a measurement atmosphere. The amount of ammonia is measured during a temperature increasing process to 700° C. at a temperature increasing rate of 10° C./min. The resulting amount of ammonia is regarded as a solid acid amount. In the measurement of the amount of ammonia, a TCD detector may be used.

It is preferable that the pentasil-type zeolite of this embodiment have a pore volume (pv) of 0.60 mL/g or less, more preferably 0.55 mL/g or less, and further preferably 0.50 mL/g or less (preferably pv≤0.60 mL/g, more preferably pv≤0.55 mL/g, and still more preferably pv≤0.50 mL/g). When the pore volume falls within this range, the packing property of the pentasil-type zeolite of this embodiment tends to be high. In addition to this, the strength of a powder of the pentasil-type zeolite of the embodiment or a molded body formed by molding the powder becomes higher, and thus the operability (handling) is likely to be higher.

In this embodiment, it is preferable that the pore volume be a value determined from an adsorption isotherm of nitrogen determined by a relative pressure method. It is more preferable that the pore volume be determined from a value obtained by multiplying a nitrogen adsorption amount at 77 K and a relative pressure p/p0 of 0.96 by a conversion factor (0.00156).

The pentasil-type zeolite of this embodiment may have mesopores. The mesopores have a larger pore diameter than that of the pores present in the crystal of the pentasil-type zeolite. The presence of the mesopores in the pentasil-type zeolite of this embodiment increases the catalytic activity of the pentasil-type zeolite. For example, the pentasil-type zeolite of the embodiment has a mesopore volume (mpv) of 0.5 mL/g or less, and preferably 0.4 mL/g or less (mpv≤0.5 mL/g, and preferably mpv≤0.4 mL/g). The mesopore volume is usually 0.05 mL/g or more (mpv≥0.05 mL/g), particularly 0.1 mL/g or more (mpv≥0.1 mL/g), and further particularly 0.15 mL/g or more (mpv≥0.15 mL/g). Herein, the mesopores are pores having a pore diameter of 2 to 50 nm that are defined by the IUPAC. In this embodiment, it is preferable that the mesopores be a value determined from a desorption isotherm of nitrogen determined by a relative pressure method. In this embodiment, it is preferable that the mesopore volume be a value determined from a desorption isotherm of nitrogen at 77 K and a pressure range that is a relative pressure from 0.38 to 0.96 at p/p0 by a BJH method.

The pentasil-type zeolite of this embodiment has the above-described acid amount. Therefore, the molar ratio of silica to alumina in the pentasil-type zeolite of this embodiment (hereinafter referred to as "$SiO_2/Al_2O_3$ ratio") is, for example, less than 150 ($SiO_2/Al_2O_3$ ratio <150). As the $SiO_2/Al_2O_3$ ratio is lower, the acid amount tends to be higher. It is preferable that the $SiO_2/Al_2O_3$ ratio of the pentasil-type zeolite of this embodiment be less than 110, more preferably less than 100, further preferably 95 or less, and still more preferably 90 or less ($SiO_2/Al_2O_3$ ratio <110, more preferably $SiO_2/Al_2O_3$ ratio <100, further preferably $SiO_2/Al_2O_3$ ratio ≤95, and still more preferably $SiO_2/Al_2O_3$ ratio ≤90).

Most aluminum (Al) in the crystal of the pentasil-type zeolite is tetra-coordinated aluminum (hereinafter referred to as "tetra-coordinated Al") or hexa-coordinated aluminum (hereinafter referred to as "hexa-coordinated Al"). As the number of the tetra-coordinated Al is larger, the number of Bronsted acid point is larger. Therefore, it is preferable that the pentasil-type zeolite of the embodiment have a larger number of tetra-coordinated Al. In the pentasil-type zeolite of this embodiment, the molar ratio of the tetra-coordinated Al to the sum of the tetra-coordinated Al and the hexa-coordinated Al (hereinafter referred to as "tetra-coordinated Al ratio") is preferably 90% or more, and more preferably 95% or more (preferably tetra-coordinated Al ratio ≥90%, and more preferably tetra-coordinated Al ratio ≥95%). Since the tetra-coordinated Al ratio is a ratio of the tetra-coordinated Al in aluminum of the crystal, the ratio is 100% or less (tetra-coordinated Al ratio ≤100%). In this embodiment, the tetra-coordinated Al ratio is a value determined by the following equation.

Tetra-coordinated Al ratio (%)={tetra-coordinated Al/(tetra-coordinated Al+hexa-coordinated Al)}×100

In the equation, tetra-coordinated Al is an area of a peak at 55±5 ppm in $^{27}$Al-NMR, and hexa-coordinated Al is an area of a peak at 0±5 ppm in $^{27}$Al-NMR.

The pentasil-type zeolite of this embodiment may contain phosphorus derived from a raw material.

Therefore, the molar ratio of phosphorus to silicon and aluminum in the pentasil-type zeolite of this embodiment (hereinafter referred to as "P/(Si+Al) ratio") is preferably 0.0005 or more, more preferably 0.001 or more, and further preferably 0.002 or more (preferably P/(Si+Al) ratio ≥0.0005, more preferably P/(Si+Al) ratio ≥0.0001, and still more preferably P/(Si+Al) ratio ≥0.0005). The P/(Si+Al) ratio in the pentasil-type zeolite of this embodiment may be 0.05 or less (P/(Si+Al) ratio ≤0.05), and particularly 0.045 or less (P/(Si+Al) ratio ≤0.045). When the P/(Si+Al) ratio is 0.01 or less (P/(Si+Al) ratio ≤0.01), the aromatic hydrocarbon selectivity tends to be higher.

The pentasil-type zeolite of the embodiment may contain an alkali metal. When the pentasil-type zeolite contains an alkali metal, the molar ratio of the alkali metal to aluminum in the pentasil-type zeolite of this embodiment (hereinafter referred to as "M/Al ratio") may be 0.5 or less (M/Al ratio 0.5), 0.4 or less (M/Al ratio ≤0.4), particularly 0.35 or less (M/Al ratio ≤0.35), and further particularly 0.2 or less (M/Al ratio ≤0.2). The alkali metal may be at least one selected from the group consisting of lithium, sodium, potassium, rubidium, and cesium. It is preferable that the alkali metal be at least one of sodium and potassium.

For example, primary particles of the pentasil-type zeolite of this embodiment have a thin-layered shape, and the thickness thereof is 10 nm or less.

In the pentasil-type zeolite of this embodiment, for example, such thin-layered primary particles aggregate to form secondary particles having an aggregate diameter of 0.3 to 50 μm. In the secondary particles of the pentasil-type zeolite of this embodiment, for example, the primary particles randomly aggregate, that is, the primary particles aggregate without regularity. When the primary particles thus aggregate without regularity, the pentasil-type zeolite of this embodiment forms secondary particles having irregular mesopores between the primary particles. It is considered that this makes it easy to diffuse an aromatic hydrocarbon and the like between the mesopores.

The irregular aggregation of the primary particles of the pentasil-type zeolite of this embodiment can be confirmed on the basis of an XRD pattern thereof. Therefore, the regular aggregation of the primary particles can be confirmed from a peak between d=2.9 to 8.8 nm in the XRD pattern thereof. Accordingly, the pentasil-type zeolite of this embodiment does not substantially have an XRD peak between d=2.9 to 8.8 nm in the XRD pattern thereof. Provided that d=2.9 to 8.8 nm corresponds to a diffraction angle 2θ=1.0 to 3.0 in the XRD pattern using a CuKα ray as a radiation source.

Note that in a pentasil-type zeolite that is obtained by crystallization of a mixture including a silica source in which silica is regularly arranged, such as mesoporous silica, and a pentasil-type zeolite that is obtained by crystallization of a mixture containing an organic surfactant having a plurality of ammonium functional groups as an SDA, primary particles are likely to be regularly arranged. Such pentasil-type zeolites have an XRD peak between d=2.9 to 8.8 nm in XRD patterns thereof.

The pentasil-type zeolite of this embodiment can be used as a catalyst, for example, a catalyst for synthesis of a hydrocarbon. As one example, the pentasil-type zeolite of this embodiment can be used as a catalyst for synthesis of an alkene having 2 to 4 carbon atoms or a catalyst for synthesis of an aromatic hydrocarbon. In addition, the pentasil-type zeolite of this embodiment is preferably used as a catalyst for synthesis of a monocyclic aromatic hydrocarbon. The monocyclic aromatic hydrocarbon is a hydrocarbon containing a benzene ring other than a condensed benzene ring. The monocyclic aromatic hydrocarbon is preferably an aromatic hydrocarbon including at least one of benzene and an alkylbenzene, and further preferably an aromatic hydrocarbon having 6 to 9 carbon atoms including at least one of benzene and an alkylbenzene. The alkylbenzene is a hydrocarbon including a benzene ring having at least one of an alkyl group and a cycloalkyl group. It is more preferable that the monocyclic aromatic hydrocarbon be at least one or more selected from the group consisting of benzene, toluene, xylene, ethylbenzene, styrene, butylbenzene, and indane.

When the pentasil-type zeolite of this embodiment is used as the catalyst, the pentasil-type zeolite may be brought into contact with a raw material compound by any method.

When the pentasil-type zeolite of this embodiment is used as the catalyst for synthesis of an alkene having 2 to 4 carbon atoms, the raw material compound may be at least one selected from the group consisting of methanol, ethanol, dimethyl ether, ethylene, and an alkene having 4 or more carbon atoms.

When the pentasil-type zeolite of this embodiment is used as the catalyst for synthesis of an aromatic hydrocarbon, the raw material compound may be at least one selected from the group consisting of an alkane, an alkene, an alcohol, gas oil, and cracked gasoline. The alkane may be at least one selected from the group consisting of methane, ethane, propane, butane, and pentane. The alkene may be at least one selected from the group consisting of ethylene, propylene, butene, and pentene. The alcohol may be at least one of methanol and ethanol. The light oil may be at least one selected from the group consisting of light cycle oil, crude gas oil, light gas oil, and hydrogenated gas oil. The light cycle oil, crude gas oil, light gas oil, and hydrogenated gas oil may contain tetralin.

For example, when the light cycle oil is used as the raw material compound to synthesize an aromatic hydrocarbon, the light cycle oil is vaporized and brought into contact with the pentasil-type zeolite of this embodiment to cause a catalytic reaction. A sa result, the aromatic hydrocarbon can be obtained. Conditions of the catalytic reaction may be a temperature of 300 to 600° C., a pressure of 0.1 to 10 MPa, and a weight hourly space velocity (WHSV) of 0.001 to 0.1/hour.

Next, a method for manufacturing the pentasil-type zeolite of this embodiment will be described.

The crystallization behavior of a pentasil-type zeolite having a high acid amount is difficult to control. Therefore, by a conventional method for manufacturing a pentasil-type zeolite, the pentasil-type zeolite that combines a higher BET specific surface area and a higher acid amount cannot be obtained. On the other hand, the inventors have found that the alkali metal in the mixture as a raw material largely influences the crystallization behavior of the pentasil-type zeolite. In addition, the inventors have found a method for manufacturing the pentasil-type zeolite that combines a higher BET specific surface area and a higher acid amount by focusing the alkali metal in the raw material and controlling the amount of the alkali metal in the co-presence of tetrabutylsulfonium cations and the alkali metal.

The manufacturing method relates to a method for manufacturing a pentasil-type zeolite including a crystallization step of crystallizing a mixture containing tetrabutylphosphonium cations, a silica source, an alumina source, an alkali metal source, and water, and the molar ratio of the alkali metal to silica in the mixture is more than 0.04 and less than 0.10.

In the crystallization step of this embodiment, the mixture (hereinafter referred to as "raw material mixture") containing tetrabutylsulfonium cations (hereinafter referred to as "TPB"), a silica source, an alumina source, an alkali metal source, and water is crystallized to obtain the pentasil-type zeolite. TBP functions as a structure directing agent. When the raw material mixture containing TBP is crystallized, the primary particles of the pentasil-type zeolite are thin-layered. Thus, the pentasil-type zeolite that can be obtained has a higher BET specific surface area than that of the conventional one.

To sufficiently achieve the effect of the structure directing agent, the molar ratio of TBP to silica in the raw material mixture (hereinafter referred to as "TBP/SiO$_2$ ratio") is preferably 0.04 or more and 0.3 or less, and more preferably 0.1 or more and 0.25 or less (preferably 0.04≤TBP/SiO$_2$ ratio ≤0.3, and more preferably 0.1≤TBP/SiO$_2$ ratio ≤0.25).

The heat of combustion of TBP is low. For this reason, even when TBP is removed by combustion from the pentasil-type zeolite obtained in the crystallization step, a thermal load to a zeolite skeleton, particularly a change from the tetra-coordinated Al to the hexa-coordinated Al due to combustion of TBP, that is, de-alumination is unlikely to occur. Therefore, the acid amount of the pentasil-type zeolite obtained by the manufacturing method of this embodiment is likely to be higher. Since TBP does not have an action of increasing mesopores unlike the organic surfactant having a plurality of ammonium functional groups, the pore volume is not too large. TBP is preferred also as a structure directing agent for obtaining a pentasil-type zeolite having an appropriate pore volume.

It is preferable that TBP be contained in the raw material mixture as a compound containing TBP (hereinafter referred to as "TBP source"). A preferable TBP source may be at least one selected from the group consisting of tetrabutylphosphonium hydroxide (hereinafter referred to as "TBPOH"), tetrabutylphosphonium chloride (hereinafter referred to as "TBPCl"), and tetrabutylphosphonium bromide (herein after referred to as "TBPBr"), and more preferably TBPOH.

In the crystallization step of this embodiment, it is not necessary that one or more of a structure directing agent other than TBP, for example, tetrapropylammonium cations (hereinafter referred to as "TPA"), tetrabutylammonium cations (hereinafter referred to as "TBA"), and another organic surfactant having a plurality of ammonium functional groups be contained. It is preferable that they be not contained.

In the crystallization step of this embodiment, a thin-layered pentasil-type zeolite having not only a higher BET specific surface area but also a higher acid amount can be obtained by controlling the alkali metal source in the raw material mixture. The molar ratio of the alkali metal to silica in the raw material mixture (hereinafter referred to as "$M/SiO_2$ ratio." M is an alkali metal) is more than 0.04 and less than 0.1 (0.04<$M/SiO_2$ ratio <0.1). When the $M/SiO_2$ ratio is 0.04 or less, the pentasil-type zeolite having an acid amount of this embodiment is unlikely to be obtained. In contrast, a pentasil-type zeolite having a low acid amount is easily crystallized unlike the pentasil-type zeolite having a high acid amount. Therefore, even when a raw material mixture in which the $M/SiO_2$ ratio is 0.04 or less is crystallized to obtain a pentasil-type zeolite, the pentasil-type zeolite has a high molar ratio of silica to alumina ($SiO_2/Al_2O_3$ ratio) of 150 or more and a low acid amount. When the $M/SiO_2$ ratio in the mixture is 0.1 or more, only a pentasil-type zeolite having a low BET specific surface area is obtained. Since the pentasil-type zeolite to be obtained has a higher BET specific surface area and a higher acid amount, the $M/SiO_2$ ratio in the raw material mixture is preferably 0.045 or more, and more preferably 0.05 or more (preferably $M/SiO_2$ ratio ≥0.045, and more preferably $M/SiO_2$ ratio ≥0.05). The $M/SiO_2$ ratio may be 0.8 or less ($M/SiO_2$ ratio ≤0.8), and particularly 0.65 or less ($M/SiO_2$ ratio ≤0.65).

The alkali metal in the raw material mixture promotes three-dimensional growth of primary particles of the crystallized pentasil-type zeolite. However, in the crystallization step of the embodiment, the three-dimensional growth of primary particles of the pentasil-type zeolite is suppressed to obtain a thin-layered pentasil-type zeolite since the $M/SiO_2$ ratio is 0.045 or more and 0.8 or less (0.045≤$M/SiO_2$ ratio ≤0.8), and particularly 0.045 or more and 0.65 or less (0.045≤$M/SiO_2$ ratio ≤0.65).

The alkali metal may be at least one selected from the group consisting of lithium, sodium, potassium, rubidium, and cesium. It is preferable that the alkali metal be at least one of sodium and potassium, and more preferably sodium.

The alkali metal source is a compound containing the alkali metal. The alkali metal source may be at least one selected from the group consisting of a hydroxide, a chloride, a bromide, a sulfide, and a silicate that contain the alkali metal, and specifically a hydroxide containing the alkali metal. When the alkali metal is sodium, a sodium source is a compound containing sodium (Na). The compound containing sodium (Na) may be at least one selected from the group consisting of sodium hydroxide, sodium chloride, sodium bromide, sodium sulfate, sodium silicate, sodium aluminate, and sodium contained as counter cations of another component. When the alkali metal is potassium, a potassium source is a compound containing potassium (K). The compound containing potassium (K) may be at least one selected from the group consisting of potassium hydroxide, potassiumchloride, potassiumbromide, potassium sulfate, potassium silicate, potassium aluminate, and potassium contained as counter cations of another component.

In addition to the TBP source and the alkali metal source, the raw material mixture contains a silica source, an alumina source, and water. When the raw material mixture containing them is crystallized, the pentasil-type zeolite of this embodiment is obtained. Therefore, the raw material mixture is not limited as long as it contains the TBP source, the alkali metal source, the silica source, the alumina source, and water. It is preferable that the raw material mixture do not contain an addition component. The addition component may be at least one kind of alcohol selected from the group consisting of methanol, ethanol, and propanol.

The silica source is a compound containing a silicon (Si). The silica source may be at least one selected from the group consisting of tetraethoxysilane, silica sol, fumed silica, precipitated silica, amorphous silica and amorphous aluminosilicate. It is preferable that the silica source be at least one selected from the group consisting of silica sol, fumed silica, precipitated silica, amorphous silica, and amorphous aluminosilicate since they are suited for industrial manufacture. It is more preferable that the silica source be silica other than mesoporous silica. The mesoporous silica may be, for example, at least one selected from the group consisting of MCM-41, MCM-48, FSM-16, and SBA-15.

The alumina source is a compound containing aluminum (Al). The alumina source may be at least one selected from the group consisting of aluminum isopropoxide, aluminum sulfate, aluminum chloride, aluminum hydroxide, pseudo-boehmite, alumina sol, and amorphous aluminosilicate. It is preferable that the alumina source be at least one selected from the group consisting of aluminum sulfate, aluminum chloride, aluminum hydroxide, pseudoboehmite, alumina sol, and amorphous aluminosilicate since they are suited for industrial manufacture.

A composition of the raw material mixture contains TBP and the rest of the composition may be any composition as long as the aforementioned $M/SiO_2$ ratio is satisfied. It is preferable that the composition of the raw material mixture be the following composition A, and more preferably the following composition B.

Composition A:
  $SiO_2/Al_2O_3$ of 40 or more and 200 or less (40≤$SiO_2/Al_2O_3$≤200)
  $TBP/SiO_2$ of 0.04 or more and 0.3 or less (0.04≤$TBP/SiO_2$≤0.3)
  $SO_4/SiO_2$ of 0 or more and 0.1 or less (0≤$SO_4/SiO_2$≤0.1)
  $OH/SiO_2$ of 0.05 or more and 0.5 or less (0.05≤$OH/SiO_2$≤0.5)
  $H_2O/SiO_2$ of 5 or more and 40 or less (5≤$H_2O/SiO_2$≤40)
  $M/SiO_2$ of more than 0.04 and less than 0.1 (0.04<$M/SiO_2$<0.1)

Composition B:
  $SiO_2/Al_2O_3$ of 50 or more and 150 or less, and particularly 60 or more and 150 or less (50≤$SiO_2/Al_2O_3$≤150, and more preferably 60≤$SiO_2/Al_2O_3$≤150)
  $TBP/SiO_2$ of 0.1 or more and 0.25 or less (0.1≤$TBP/SiO_2$≤0.25)
  $SO_4/SiO_2$ of 0.02 or more and 0.05 or less (0.02≤$SO_4/SiO_2$≤0.05)
  $OH/SiO_2$ of 0.15 or more and 0.2 or less (0.15≤$OH/SiO_2$≤0.2)
  $H_2O/SiO_2$ of 5 or more and 15 or less (5≤$H_2O/SiO_2$≤15)

M/SiO$_2$ of more than 0.04 and less than 0.1, and particularly 0.05 or more and 0.8 or less (0.04<M/SiO$_2$<0.1, and more preferably 0.05≤M/SiO$_2$≤0.8)

The above-described compositions are the molar composition of each component.

In the crystallization step, the raw material mixture is crystallized. As a result, the raw material mixture is converted into the pentasil-type zeolite. Conditions are arbitrary as long as the raw material mixture is crystallized. Specifically, the raw material mixture can be treated at a temperature of 40° C. or higher and 200° C. or lower, and particularly 90° C. or higher and 140° C. or lower for any time. The treatment time is a time sufficient for crystallization, for example, 24 hours or more and 240 hours or less, and preferably 50 hours or more and 90 hours or less.

The manufacturing method of this embodiment may include a washing step, a drying step, and a TBP removal step after the crystallization step.

In the washing step, the pentasil-type zeolite obtained in the crystallization step is subjected to solid-liquid separation to obtain a crystallized product as a solid phase. A washing method is arbitrary. The crystallized product may be washed with pure water.

In the drying step, the pentasil-type zeolite obtained as a crystal is dried. A drying method may be a treatment at 100 to 200° C. in the air.

In the TBP removal step, TBP is removed. In the crystallization step, the pentasil-type zeolite containing TBP is obtained. From such a pentasil-type zeolite containing TBP (hereinafter referred to as "TBP-containing pentasil-type zeolite"), TBP can be removed as appropriate. Examples of a method for removing TBP may include calcining and decomposition. When TBP is removed by calcining, the TBP-containing pentasil-type zeolite is treated at 400 to 800° C., and particularly 500 to 700° C. for 0.5 to 12 hours under the flow of oxygen-containing gas.

In the TBP removal step, the pentasil-type zeolite after the removal of TBP by calcining or decomposition may be washed again. As a result, remaining P and Na may be reduced or removed. Examples of a washing method at that time may include mixing of at least one selected from the group consisting of water, an aqueous ammonium chloride solution, dilute hydrochloric acid, dilute sulfuric acid, and dilute nitric acid with the pentasil-type zeolite after the removal of TBP. The mixed pentasil-type zeolite may be washed by any method such as washing with pure water.

According to this embodiment, the pentasil-type zeolite that combines a higher BET specific surface area and a higher acid amount than those of conventional ones and the method for manufacturing the same can be provided.

The pentasil-type zeolite of this embodiment has a higher BET specific surface area and a higher solid acid amount. Therefore, a high activity, a high yield, and a long lifetime during use of the pentasil-type zeolite as a catalyst as well as high adsorption during use of the pentasil-type zeolite as an adsorbent or high ion exchange rate during use of the pentasil-type zeolite as an ion exchanger can be expected.

Since the pentasil-type zeolite of this embodiment has an appropriate pore volume, the pentasil-type zeolite may act as a catalyst having excellent operability (handling) and high packing property.

The pentasil-type zeolite of this embodiment can be used as a catalyst for synthesis of an aromatic hydrocarbon or a catalyst for synthesis of a monocyclic aromatic hydrocarbon that has a high yield and a high selectivity. Furthermore, when the pentasil-type zeolite of this embodiment is used as a catalyst for manufacturing an alkene having 2 to 4 carbon atoms such as propylene from a lower hydrocarbon having 1 to 5 carbon atoms such as ethanol, ethylene, methanol, and dimethyl ether, a catalyst for an additive for increasing the production of propylene by fluid catalytic cracking, a catalyst for catalytic cracking of naphtha, or the like, the pentasil-type zeolite can be expected to act as a catalyst that achieves a high activity, a high yield, and a long lifetime.

EXAMPLES

Hereinafter, the present invention will be described specifically with reference to Examples. However, the present invention is not limited to these Examples.

Respective measurement methods in Examples and Comparative Examples are as follows.

(Identification of Crystal Structure)

A powder X-ray diffraction of a sample was measured by a general X-ray diffractometer (trade name: MXP-3, manufactured by MAC Science Co. Ltd.). Measurement conditions are as follows.

Radiation source: CuKα-ray (λ=1.5405 Å)
Measurement mode: step scan
Scan condition: 0.02°/second
Divergence slit: 1.0 deg
Scattering slit: 1.0 deg
Receiving slit: 0.3 mm
Measurement time: 1 second
Measurement range: 2θ=30 to 43°

The sample was identified by comparison of the obtained XRD pattern with an XRD pattern described in Collection of simulated XRD powder patterns for zeolites, Fifth revised edition, p. 483 (2007).

(Measurement of Mesopores)

A state of mesopores was determined by powder X-ray diffraction measurement of the sample by a general X-ray diffractometer (trade name: MXP-3, manufactured by MAC Science Co. Ltd.). Measurement conditions are as follows.

Radiation source: CuKα-ray (λ=1.5405 Å)
Measurement mode: step scan
Scan condition: 0.02°/second
Divergence slit: 0.5 deg
Scattering slit: 0.5 deg
Receiving slit: 0.15 mm
Measurement time: 0.2 seconds or 5.0 seconds
Measurement range: 2θ=1° to 3° or 1.26° to 3°

The state of the mesopores was confirmed from the presence or absence of a peak in the obtained XRD pattern.

(Observation of Form)

A form of the sample was observed by a scanning electron microscope (hereinafter referred to as "SEM") or a transmission electron microscope (hereinafter referred to as "TEM"). In the observation by SEM, a field emission scanning electron microscope (trade name: S-4500, manufactured by Hitachi, Ltd.) was used. In the observation by TEM, a transmission electron microscope (trade name: JEM-2000FXII, manufactured by JEOL Ltd.) was used.

(Composition Analysis)

A composition was analyzed by inductively coupled plasma emission spectroscopy (ICP method). The sample was dissolved in a mixed solution of hydrofluoric acid and nitric acid to prepare a measurement solution. The resulting measurement solution was measured by a general inductively coupled plasma emission spectrometer (trade name: OPTIMA3000DV, manufactured by PerkinElmer Inc.), to analyze the composition of the sample.

(BET Specific Surface Area)

A BET specific surface area of the sample was determined by measurement in accordance with JIS8830. In the measurement, a general specific surface area measurement device (trade name: FlowSorb III, manufactured by Shimadzu Corporation) was used. For pretreatment, the sample was held at 400° C. for 2 hours. The BET specific surface area of the pretreated sample was measured. Measurement conditions are as follows.

Treatment gas: mixed gas containing 30% by volume of nitrogen and 70% by volume of helium (corresponding to a relative pressure p/p0 of 0.3)

Measurement method: single point method (Pore Volume)

A total pore volume was measured by measurement of nitrogen adsorption isotherm. In the measurement, a general adsorption amount measurement device (trade name: BELSORP28SA, manufactured by BEL JAPAN, INC.) was used. For pretreatment, the sample was held at 350° C. for 2 hours. The nitrogen adsorption isotherm of the pretreated sample was measured. Measurement conditions are as follows.

Treatment gas: nitrogen gas

Treatment Temperature: temperature of liquid nitrogen

Measurement pressure: $10^{-4}$ kPa to 100 kPa (corresponding to a relative pressure p/p0 of $10^{-6}$ to 1.0)

The total pore volume of the sample was determined from a nitrogen adsorption amount corresponding to a relative pressure p/p0 of $10^{-6}$ to $9.6 \times 10^{-1}$ in the obtained adsorption isotherm.

(Measurement of Mesopore Volume)

The mesopore volume was measured by measurement of nitrogen adsorption isotherm. In the measurement, a general adsorption amount measurement device (trade name: BELSORP28SA, manufactured by BEL JAPAN, INC.) was used. For pretreatment, the sample was held at 350° C. for 2 hours. The nitrogen desorption isotherm of the pretreated sample was measured. Measurement conditions are as follows.

Treatment gas: nitrogen gas

Treatment Temperature: temperature of liquid nitrogen

Measurement pressure: 100 kPa to $10^{-4}$ kPa (corresponding to a relative pressure p/p0 of 1.0 to $10^{-6}$)

The mesopore volume of the sample was determined by a BJH method from a nitrogen desorption amount corresponding to a relative pressure p/p0 of $9.6 \times 10^{-1}$ to $1.0 \times 10^{-6}$ in the obtained adsorption isotherm.

(Analysis of Al State)

A tetra-coordinated Al ratio was determined by $^{27}$Al-NMR. In the measurement, a general nuclear magnetic resonance spectrometer (trade name: VNMRS-400, manufactured by Varian, Inc.) was used. For pretreatment, the sample was held in a state of relative humidity of 80% overnight. $^{27}$Al-NMR measurement was performed using the pretreated sample under the following conditions to obtain a NMR pattern.

Rotation frequency: 15 kHz

State of sample tube: rotation

The resulting NMR pattern was subjected to background processing. An area of a peak at 55±5 ppm was regarded as tetra-coordinated Al, an area of a peak at 0±5 ppm was regarded as hexa-coordinated Al, and a tetra-coordinated Al ratio was determined by the following equation.

Tetra-coordinated Al ratio (%)={tetra-coordinated Al/(tetra-coordinated Al+hexa-coordinated Al)}×100

(Measurement of Solid Acid Amount)

The solid acid amount of the sample was measured by an ammonia-TPD method.

0.1 g of the sample was allowed to stand under flow of helium of 500° C., which was regarded as pretreatment. A mixed gas containing 10% by volume of ammonia and 90% by volume of helium was passed through the sample at room temperature after the pretreatment for 1 hour. Thus, the sample was saturated with ammonia to allow ammonia to be adsorbed to the sample. After the passing of the mixed gas for 1 hour, the sample was heated to 100° C. while helium was passed therethrough instead of the mixed gas. After the heating, helium gas was passed at 100° C. for 1 hour to remove ammonia remaining in the atmosphere.

After the removal of the remaining ammonia, the temperature was increased to 700° C. at a temperature increasing rate of 10° C./min under flow of helium at a flow rate of 50 mL/min. The ammonia amount was measured using a TCD detector during the temperature increasing process. The measured ammonia amount was regarded as an amount of ammonia adsorbed on the sample. A solid acid amount (mmol/g) was an adsorption ammonia amount per unit mass of the sample.

Example 1

An aqueous sodium silicate solution and a sulfuric acid were mixed to obtain amorphous particulate silica. The obtained amorphous particulate silica, aluminum sulfate, a 40% TBPOH aqueous solution, sodium hydroxide, and pure water were mixed to obtain a raw material mixture having the following composition:

$SiO_2/Al_2O_3$=100,
$TBP/SiO_2$=0.20,
$Na/SiO_2$=0.05,
$SO_4/SiO_2$=0.03,
$OH/SiO_2$=0.19, and
$H_2O/SiO_2$=10.

A reaction vessel made of stainless was filled with the obtained raw material mixture, and sealed. After that, the reaction vessel was heated to 130° C. under revolution at 55 rpm. After the heating, the reaction vessel was held at 130° C. for 72 hours while the revolution was maintained. Thus, the raw material mixture was crystallized to obtain a crystallized slurry.

The crystallized slurry was cooled, filtered, washed, and dried at 110° C. to obtain a crystallized product.

The crystallized product was a pentasil-type zeolite, and did not contain a structure other than a pentasil structure. The pentasil-type zeolite formed secondary particles of aggregates in which thin-layered crystals (primary particles) aggregated. The secondary particles had a particle diameter of 0.4 μm. The XRD pattern did not have a substantial peak between 2θ=1.0 to 3.0 (note that the XRD patterns of crystallized products obtained in other Examples were the same).

Figure 2:
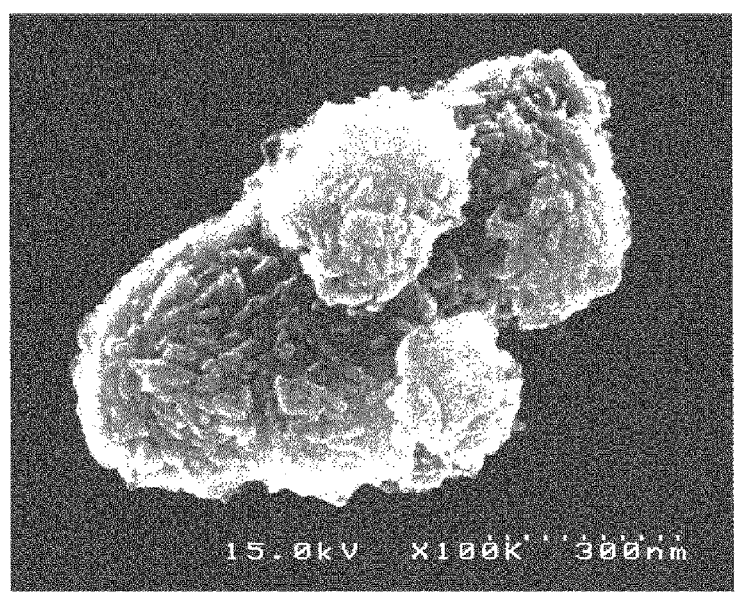
FIG. 2 is a view in which the crystallized pentasil-type zeolite obtained in Example 1 is observed by a scanning electron microscope (the scale is 300 nm).

FIG. 1 shows the XRD pattern in which the crystalline phase of the crystallized product was identified, and FIG. 2 shows a view in which the product was observed by SEM.

The obtained pentasil-type zeolite was calcined at 550° C. in the air, which was regarded as a pentasil-type zeolite of Example 1. The pentasil-type zeolite of Example 1 had a pore volume of 0.47 mL/g. The evaluation results are shown in Table 1.

Example 2

A pentasil-type zeolite was obtained by crystallization, cooling, filtration, washing, drying, and calcining in the same manner as in Example 1. The obtained pentasil-type zeolite and 2 L of pure water were mixed at 70° C., filtered, and dried to obtain a pentasil-type zeolite of Example 2. The pentasil-type zeolite of Example 2 had a pore volume of 0.47 mL/g. The evaluation results are shown in Table 1.

Example 3

An aqueous sodium silicate solution and an aqueous aluminum sulfate solution were mixed so that a $SiO_2/Al_2O_3$ ratio was 100. The resulting mixture was dehydrated and washed to obtain amorphous particulate aluminosilicate ($SiO_2/Al_2O_3=100$).

The obtained amorphous particulate aluminosilicate, a 40% TBPOH aqueous solution, sodium hydroxide, sulfuric acid, and pure water were mixed to obtain a raw material mixture having the following composition:
$SiO_2/Al_2O_3=100$,
$TBP/SiO_2=0.20$,
$Na/SiO_2=0.05$,
$SO_4/SiO_2=0.03$,
$OH/SiO_2=0.19$, and
$H_2O/SiO_2=10$.

The raw material mixture was crystallized, cooled, filtered, washed, and dried in the same manner as in Example 1. Thus, a crystallized product was obtained. The crystallized product was a pentasil-type zeolite, and did not contain a structure other than a pentasil structure.

The obtained pentasil-type zeolite was calcined at 550° C. in the air, which was regarded as a pentasil-type zeolite of Example 3. The pentasil-type zeolite of Example 3 had a pore volume of 0.45 mL/g. The evaluation results are shown in Table 1.

Example 4

An amorphous silica was obtained in the same manner as in Example 1. The obtained amorphous particulate silica, aluminum sulfate, a 40% TBPOH aqueous solution, sodium hydroxide, and pure water were mixed to obtain a raw material mixture having the following composition:
$SiO_2/Al_2O_3=80$,
$TBP/SiO_2=0.20$,
$Na/SiO_2=0.05$,
$SO_4/SiO_2=0.04$,
$OH/SiO_2=0.18$, and
$H_2O/SiO_2=10$.

Figure 3:
FIG. 3 is a view in which a crystallized pentasil-type zeolite obtained in Example 4 is observed by a transmission electron microscope.

The raw material mixture was crystallized, cooled, filtered, washed, and dried in the same manner as in Example 1. Thus, a crystallized product was obtained. The crystallized product was a zeolite having a pentasil structure, and did not contain a structure other than the pentasil structure. FIG. 3 shows a view in which the crystallized product was observed by TEM.

The obtained zeolite was calcined at 550° C. in the air, which was regarded as a pentasil-type zeolite of Example 4. The pentasil-type zeolite of Example 4 had a pore volume of 0.46 mL/g and a mesopore volume of 0.37 mL/g. The evaluation results of the pentasil-type zeolite of Example 4 are shown in Table 1.

Example 5

A pentasil-type zeolite was obtained by crystallization, cooling, filtration, washing, drying, and calcining in the same manner as in Example 4. The obtained pentasil-type zeolite and 2 L of pure water were mixed at 70° C., filtered, and dried to obtain a pentasil-type zeolite of Example 5.

Figure 4:
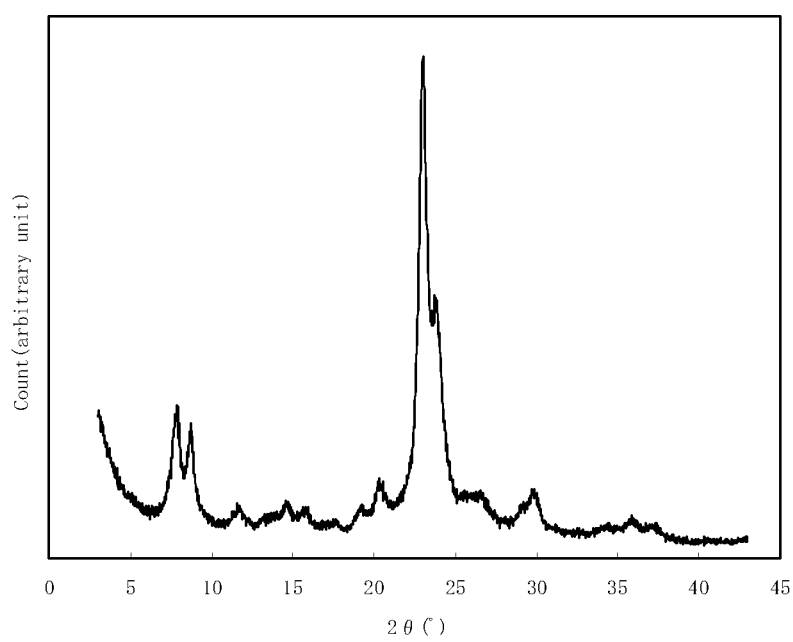
FIG. 4 is a powder X-ray diffraction diagram of a pentasil-type zeolite obtained in Example 5.
Figure 5:
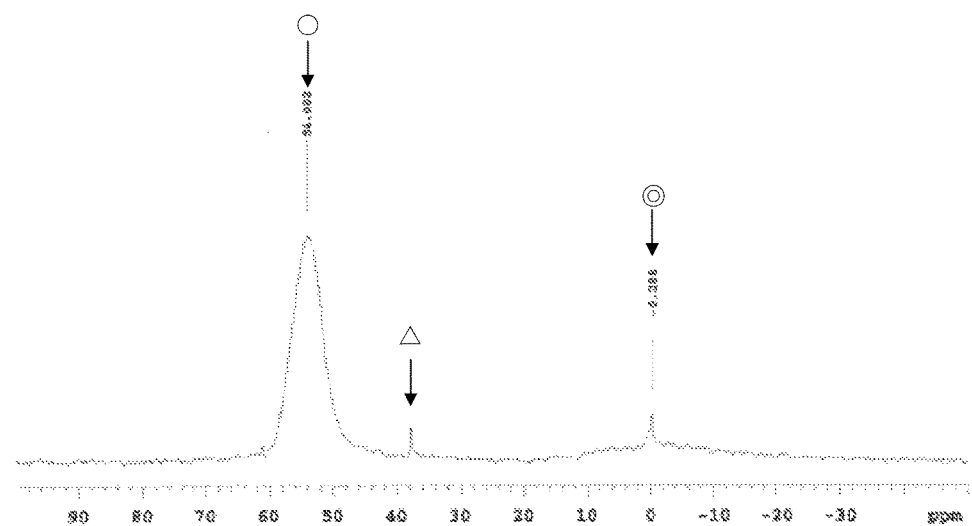
FIG. 5 is a $^{27}Al$-NMR spectrum of the pentasil-type zeolite obtained in Example 5.

The pentasil-type zeolite of Example 5 had a pore volume of 0.44 mL/g. The evaluation results are shown in Table 1. The results of identification of a crystalline phase are shown in FIG. 4 and the $^{27}$Al-NMR spectrum is shown in FIG. 5.

The pentasil-type zeolite of Example 5 was a pentasil-type zeolite. The regular aggregation of primary particles was not confirmed. The tetra-coordinated Al ratio was 97%. This shows that most aluminum in the crystal was tetra-coordinated Al, and most aluminum in the crystal of the pentasil-type zeolite was not de-aluminated even after a downstream process such as removal of SDA.

Example 6

An amorphous silica was obtained in the same manner as in Example 1. The obtained amorphous particulate silica, aluminum sulfate, a 40% TBPOH aqueous solution, sodium hydroxide, and pure water were mixed to obtain a raw material mixture having the following composition:
$SiO_2/Al_2O_3=100$,
$TBP/SiO_2=0.20$,
$Na/SiO_2=0.06$,
$SO_4/SiO_2=0.03$,
$OH/SiO_2=0.20$, and
$H_2O/SiO_2=10$.

The raw material mixture was crystallized, cooled, filtered, washed, and dried in the same manner as in Example 1. Thus, a crystallized product was obtained. The crystallized product was a zeolite having a pentasil structure, and did not contain a structure other than a pentasil structure.

The obtained zeolite was calcined at 550° C. in the air, which was regarded as a pentasil-type zeolite of Example 6. The pentasil-type zeolite of Example 6 had a pore volume of 0.44 mL/g. The evaluation results are shown in Table 1.

Example 7

An aqueous sodium silicate solution and an aqueous aluminum sulfate solution were mixed so that a $SiO_2/Al_2O_3$ ratio was 56. The resulting mixture was dehydrated and washed to obtain amorphous particulate aluminosilicate ($SiO_2/Al_2O_3=56$). The amorphous particulate aluminosilicate was added to and mixed in a 10% KCl aqueous solution. Thus, sodium in the amorphous particulate aluminosilicate was ion-exchanged with potassium.

The ion-exchanged amorphous particulate aluminosilicate, a 40% TBPOH aqueous solution, potassium hydroxide, and pure water were mixed to obtain a raw material mixture having the following composition:
$SiO_2/Al_2O_3=56$,
$TBP/SiO_2=0.14$,
$K/SiO_2=0.06$,
$SO_4/SiO_2=0$,
$OH/SiO_2=0.20$, and
$H_2O/SiO_2=10$.

The raw material mixture was crystallized, cooled, filtered, washed, and dried in the same manner as in Example 1 except that the reaction temperature was changed to 120° C. and the time was changed to 160 hours. Thus, a crystallized product was obtained. The crystallized product was a pentasil-type zeolite, and did not contain a structure other than a pentasil structure.

The obtained pentasil-type zeolite was calcined at 550° C. in the air. The calcined pentasil-type zeolite and 2 L of pure water were mixed at 70° C., filtered, and dried to obtain a pentasil-type zeolite of Example 7. The pentasil-type zeolite of Example 7 had a pore volume of 0.39 mL/g and a mesopore volume of 0.18 mL/g. The evaluation results of the pentasil-type zeolite of Example 7 are shown in Table 1.

Comparative Example 1

A pentasil-type zeolite was synthesized in accordance with Non-Patent Literature 2. Specifically, tetraethoxysilane (Tokyo Chemical Industry Co., Ltd.), aluminum sulfate, a 40% TBPOH aqueous solution, sodium hydroxide, and pure water were mixed to obtain a raw material mixture having the following composition:
$SiO_2/Al_2O_3=200$,
$TBP/SiO_2=0.30$,
$Na/SiO_2=0.01$,
$SO_4/SiO_2=0.015$,
$OH/SiO_2=0.28$,
$H_2O/SiO_2=10$, and
$C_2H_5OH/SiO_2=4$.

A reaction vessel made of stainless was filled with the obtained raw material mixture, and sealed. After that, the reaction vessel was heated to 115° C. with standing. After the heating, the reaction vessel was held at 115° C. for 72 hours with standing. Thus, the raw material mixture was crystallized to obtain a crystallized slurry.

The crystallized slurry was cooled, filtered, washed, and dried in the same manner as in Example 1. Thus, a crystallized product was obtained. The crystallized product was a pentasil-type zeolite, and did not contain a structure other than a pentasil structure.

The pentasil-type zeolite was calcined at 550° C. in the air, which was regarded as a pentasil-type zeolite of Comparative Example 1. The evaluation results of the pentasil-type zeolite of Comparative Example 1 are shown in Table 1.

The pentasil-type zeolite of Comparative Example 1 formed secondary particles having an aggregate particle diameter of 200 nm or less. Therefore, a time required for filtration and washing was longer and the operability was poor as compared with the pentasil-type zeolites of Examples.

Comparative Example 2

A raw material mixture was obtained in the same manner as in Comparative Example 1 except for the following composition:
$SiO_2/Al_2O_3=100$,
$TBP/SiO_2=0.30$,
$Na/SiO_2=0.015$,
$SO_4/SiO_2=0.03$,
$OH/SiO_2=0.26$, and
$H_2O/SiO_2=10$.

The obtained raw material mixture was heated, cooled, filtered, washed, and dried in the same manner as in Comparative Example 1. Thus, a powdered material was obtained. In an XRD pattern of the powdered material, only a broad part was shown, and a clear peak was not shown. This confirmed that the powdered material was amorphous.

Comparative Example 3

Amorphous particulate aluminosilicate was obtained in the same manner as in Example 1. The obtained amorphous particulate silica, aluminum sulfate, a 40% TBPOH aqueous solution, sodium hydroxide, and pure water were mixed to obtain a raw material mixture having the following composition:
$SiO_2/Al_2O_3=100$,
$TBP/SiO_2=0.20$,
$Na/SiO_2=0.04$,
$SO_4/SiO_2=0.03$,
$OH/SiO_2=0.18$,
$H_2O/SiO_2=10$.

The raw material mixture was crystallized, cooled, filtered, washed, and dried in the same manner as in Example 1. Thus, a powdered material was obtained. In an XRD pattern of the powdered material, only a broad peak was shown. This confirmed that the powdered material was amorphous.

Comparative Example 4

An amorphous silica was obtained in the same manner as in Example 1. The obtained amorphous particulate silica, aluminum sulfate, a 40% TBPOH aqueous solution, sodium hydroxide, and pure water were mixed to obtain a raw material mixture having the following composition:
$SiO_2/Al_2O_3=100$,
$TBP/SiO_2=0.20$,
$Na/SiO_2=0.04$,
$SO_4/SiO_2=0.03$,
$OH/SiO_2=0.18$, and
$H_2O/SiO_2=10$.

A powdered material was obtained by crystallization, cooling, filtration, washing, and drying in the same manner as in Example 1 except that the reaction vessel was held at 130° C. for 120 hours while the revolution was maintained. In an XRD pattern of the powdered material, only a broad peak was shown. This confirmed that the powdered material was amorphous.

Comparative Example 5

Amorphous particulate aluminosilicate ($SiO_2/Al_2O_3=100$) was obtained in the same manner as in Example 3.

The obtained amorphous particulate aluminosilicate, a 40% TBPOH aqueous solution, sodium hydroxide, and pure water were mixed to obtain a raw material mixture having the following composition:
$SiO_2/Al_2O_3=100$,
$TBP/SiO_2=0.20$,
$Na/SiO_2=0.10$,
$SO_4/SiO_2=0$,
$OH/SiO_2=0.30$, and
$H_2O/SiO_2=10$.

The raw material mixture was crystallized, cooled, filtered, washed, and dried in the same manner as in Example 1. Thus, a crystallized product was obtained. The crystallized product was a pentasil-type zeolite, and did not contain a structure other than a pentasil structure.

The evaluation results of the pentasil-type zeolite of Comparative Example 5 are shown in Table 1.

Comparative Example 6

Amorphous particulate aluminosilicate was obtained in the same manner as in Example 3. The $SiO_2/Al_2O_3$ ratio of the amorphous particulate aluminosilicate obtained was 100.

The obtained amorphous particulate aluminosilicate, a 50% tetrapropylammonium bromide aqueous solution, sodium hydroxide, and pure water were mixed to obtain a raw material mixture having the following composition:
$SiO_2/Al_2O_3=100$,
$TPA/SiO_2=0.05$,
$Na/SiO_2=0.17$,
$Br/SiO_2=0.05$,
$OH/SiO_2=0.17$,
$H_2O/SiO_2=10$.

The raw material mixture was allowed to stand at 180° C. for 24 hours, resulting in crystallization. After the crystallization, the mixture was cooled, filtered, washed, and dried in the same manner as in Example 1. Thus, a crystallized product was obtained. The crystallized product was a pentasil-type zeolite, and did not contain a structure other than a pentasil structure. The obtained pentasil-type zeolite was calcined at 550° C. in the air, and mixed with 2 L of 10% ammonium chloride at 70° C. The mixture was filtered, dried, and further calcined at 500° C. to obtain a pentasil-type zeolite of Comparative Example 6. The evaluation results of the pentasil-type zeolite of Comparative Example 6 are shown in Table 1.

Comparative Example 7

Amorphous silica was obtained in the same manner as in Example 1. The obtained amorphous particulate silica, aluminum sulfate, a 40% TBPOH aqueous solution, sodium hydroxide, and pure water were mixed to obtain a raw material mixture having the following composition:
$SiO_2/Al_2O_3=200$,
$TBP/SiO_2=0.20$,
$Na/SiO_2=0.05$,
$SO_4/SiO_2=0.015$,
$OH/SiO_2=0.22$,
$H_2O/SiO_2=10$.

A reaction vessel made of stainless was filled with the obtained raw material mixture, and sealed. After that, the reaction vessel was heated to 130° C. with standing. After the heating, the reaction vessel was held at 130° C. for 72 hours with standing. Thus, the raw material mixture was crystallized to obtain a crystallized slurry.

The crystallized slurry obtained was cooled, filtered, washed, and dried in the same manner as in Example 1. Thus, a crystallized product was obtained. The crystallized product was a pentasil-type zeolite, and did not contain a structure other than a pentasil structure.

The obtained pentasil-type zeolite and 2 L of pure water were mixed at 70° C., filtered, and dried to obtain a pentasil-type zeolite of Comparative Example 7.

TABLE 1

| | CRYSTAL STRUCTURE | COMPOSITION (mol/mol) | | | BET SPECIFIC SURFACE AREA ($m^2/g$) | ACID AMOUNT (mmol/g) |
| | | $SiO_2/Al_2O_3$ | M/Al | P/(Si + Al) | | |
| --- | --- | --- | --- | --- | --- | --- |
| EXAMPLE 1 | PENTASIL | 89 | 0.38 | 0.047 | 501 | 0.45 |
| EXAMPLE 2 | PENTASIL | 107 | 0.01 | 0.002 | 584 | 0.41 |
| EXAMPLE 3 | PENTASIL | 81 | 0.34 | 0.047 | 515 | 0.42 |
| EXAMPLE 4 | PENTASIL | 74 | 0.31 | 0.048 | 523 | 0.56 |
| EXAMPLE 5 | PENTASIL | 94 | 0.12 | 0.002 | 517 | 0.52 |
| EXAMPLE 6 | PENTASIL | 98 | 0.47 | 0.044 | 467 | 0.42 |
| EXAMPLE 7 | PENTASIL | 53 | 0.13 | 0.009 | 513 | 0.58 |
| COMPARATIVE EXAMPLE 1 | PENTASIL | 167 | 0.13 | 0.035 | 560 | 0.24 |
| COMPARATIVE EXAMPLE 2 | AMORPHOUS | — | — | — | — | — |
| COMPARATIVE EXAMPLE 3 | AMORPHOUS | — | — | — | — | — |
| COMPARATIVE EXAMPLE 4 | AMORPHOUS | — | — | — | — | — |
| COMPARATIVE EXAMPLE 5 | PENTASIL | 75 | 0.62 | 0.042 | 400 | 0.53 |
| COMPARATIVE EXAMPLE 6 | PENTASIL | 85 | <0.01 | 0 | 381 | 0.48 |
| COMPARATIVE EXAMPLE 7 | PENTASIL | 196 | <0.01 | — | 528 | 0.29 |

IN TABLE, "—" REPRESENTS NOT-MEASUREMENT.

The pentasil-type zeolites obtained in these Examples had a BET specific surface area of 450 $m^2/g$ or more. The pentasil-type zeolites in Examples 1 to 5 and 7 had a high BET specific surface area of 500 $m^2/g$ or more and an acid amount of 0.4 mmol/g or more, that is, combined a high BET specific surface area and a high acid amount.

(Evaluation of Catalytic Reaction)

The pentasil-type zeolites of Example 5 and Comparative Examples 6 and 7 were evaluated as a catalyst for synthesis of an aromatic hydrocarbon. The results are shown in Table 2.

For pretreatment, the powdered sample was pressurized at 400 kgf/$cm^2$ for 1 minute to prepare an aggregate. The resulting aggregate was pulverized into pellets having a diameter of 1 mm, which were a catalyst for evaluation.

A raw material gas was passed through the catalyst for evaluation so that the amount of tetralin passed through the catalyst for evaluation was constant. Thus, tetralin was converted into a monocyclic aromatic hydrocarbon having 6 to 9 carbon atoms (hereinafter referred to as "$C_{6-9}$"). Evaluation conditions are as follows.

Raw material gas: tetralin
Carrier gas: nitrogen
Weight of catalyst for evaluation: 1.0 g
Flow rate of raw material gas: weight of tetralin/weight of catalyst=0.0354/hour
Catalytic reaction temperature: 450° C.
Pressure: 0.1 MPa The raw material gas and the gas passed through the catalyst for evaluation (hereinafter referred to as "reaction gas 1") were assayed by gas chromatography provided with a hydrogen flame ionization detector (FID) (device name: GC-14A, manufactured by Shimadzu Corporation). From the obtained results of analysis, the conversion ratio of tetralin was determined by the following equation (1), and the yield of the monocyclic aromatic hydrocarbon was determined by the following equation (2).

$$TC=\{1-(ET/IT)\}\times100 \qquad (1)$$

In the equation (1), TC is the conversion ratio (%) of tetralin, IT is the number of carbons of tetralin (mol/min) in the raw material gas, and ET is the number of carbons of tetralin (mol/min) in the reaction gas 1.

$$CA=EA/IT\times100 \qquad (2)$$

In the formula (2), CA is the yield of monocyclic aromatic hydrocarbon having 6 to 9 carbon atoms (hereinafter referred to as $C_{6-9}$), EA is the number of carbons of $C_{6-9}$ (mol/min) in the reaction gas 1, and IT is the number of carbons of tetralin (mol/min) in the raw material gas.

TABLE 2

|  | CONVERSION RATIO OF TETRALIN | YIELD OF $C_{6-9}$ |
|---|---|---|
| EXMAPLE 5 | 56% | 27% |
| COMPARATIVE EXAMPLE 6 | 31% | 17% |
| COMPARATIVE EXAMPLE 7 | 38% | 20% |

The conversion ratio of tetralin of the pentasil-type zeolite of Example 5 was higher than those of the pentasil-type zeolites of Comparative Examples 6 and 7. Thus, the pentasil-type zeolite of the present invention was confirmed to more efficiently convert tetralin into $C_{6-9}$. Further, the yield of $C_{6-9}$ of the pentasil-type zeolite of Example 5 was high. This confirmed that a target aromatic hydrocarbon was more efficiently obtained.

All the pentasil-type zeolites of Examples had a pore volume of 0.60 mL/g or less, and particularly 0.50 mL/g or less, and therefore had an appropriate pore volume. Therefore, in the catalyst of Example 5, a phenomenon in which the catalyst collapsed during evaluation of the catalyst was not observed. This confirmed that the pentasil-type zeolite of the present invention was easily handled.
(Evaluation 2 of Catalytic Reaction)

The pentasil-type zeolite of Example 5 was evaluated as a catalyst for synthesis of an alkene having 2 to 4 carbon atoms (hereinafter referred to as "$C_{2-4}$"). The results are shown in Table 3.

For pretreatment, the powdered sample was pressurized at 400 kgf/cm² for 1 minute to prepare an aggregate. The resulting aggregate was pulverized into pellets having a diameter of 1 mm, which were a catalyst for evaluation.

A raw material gas was passed through the catalyst for evaluation so that the amount of ethanol passed through the catalyst for evaluation was constant. Thus, ethanol was converted into a $C_{2-4}$. Evaluation conditions are as follows.
  Raw material gas: ethanol
  Carrier gas: nitrogen
  Weight of catalyst for evaluation: 1.0 g
  Flow rate of raw material gas: weight of ethanol/weight of catalyst=4/hour
  Catalytic reaction temperature: 400° C.
  Pressure: 0.1 MPa The raw material gas and a gas passed through the catalyst for evaluation for 20 minutes (hereinafter referred to as "reaction gas 2") were assayed by gas chromatography provided with a hydrogen flame ionization detector (FID) (device name: GC-14A, manufactured by Shimadzu Corporation). From the obtained results of analysis, the conversion ratio of ethanol was determined by the following equation (3), and the yield of the $C_{2-4}$ was determined by the following equation (4).

$$EtC=\{1-(EEt/IEt)\}\times100 \qquad (3)$$

In the equation (3), EtC is the conversion ratio (%) of ethanol, IEt is the number of carbons of ethanol (mol/min) in the raw material gas, and EEt is the number of carbons of ethanol (mol/min) in the reaction gas 2.

$$CO=EO/IEt\times100 \qquad (4)$$

In the formula (4), CO is the yield of $C_{2-4}$, EO is the number of carbons of $C_{2-4}$ (mol/min) in the reaction gas 2, and IEt is the number of carbons of ethanol (mol/min) in the raw material gas.

TABLE 3

|  | CONVERSION RATIO OF ETHANOL | YIELD | | | |
|---|---|---|---|---|---|
|  |  | ETHYLENE | PROPYLENE | BUTENE | $C_{2-4}$ |
| EXAMPLE 5 | 100% | 63% | 19% | 15% | 97% |

($C_{2-4}$ YIELD) = (ETHYLENE YIELD) + (PROPYLENE YIELD) + (BUTENE YIELD)

From Table 3, in the pentasil-type zeolite of Example 5, the conversion ratio of ethanol was 100%. This confirmed that the conversion ratio of ethanol was high. Further, the yield of $C_{2-4}$ was 97%. This confirmed that most ethanol was converted into $C_{2-4}$. As confirmed from the results, the pentasil-type zeolite of the present invention served not only as a catalyst for synthesis of an aromatic hydrocarbon, but also as a catalyst for conversion of ethanol and further as a catalyst for synthesis of a lower alkene from ethanol.

INDUSTRIAL APPLICABILITY

The pentasil-type zeolite of the present invention can be used as a catalyst, an adsorbent, an ion exchanger, or the like. In particular, the pentasil-type zeolite of the present invention can be used as a catalyst for manufacturing an aromatic hydrocarbon in manufacturing the aromatic hydrocarbon or as a selective catalyst for the aromatic hydrocarbon. In addition, the pentasil-type zeolite of the present invention can be used as a catalyst for synthesis of an alkene having 2 to 4 carbon atoms, for example, a catalyst for manufacturing propylene using an alcohol such as ethanol including bioethanol as a raw material, or a catalyst for manufacturing propylene using dimethyl ether or ethylene as a raw material. Further, the pentasil-type zeolite of the present invention can be used as a catalyst for an additive for increasing the production of propylene by fluid catalytic cracking, a catalyst for catalytic cracking of naphtha, or a catalyst for production of liquid fuel by catalytic thermal cracking of biomass.

The entire content of Japanese Patent Application No. 2013-178999 filed on Aug. 30, 2013 including specification, claims, drawings, and abstract is incorporated herein in its entirety by reference.

REFERENCE SIGNS LIST

Circle: tetra-coordinated Al
Double circle: hexa-coordinated Al
Triangle: noise

The invention claimed is:

1. A pentasil-type zeolite comprising a BET specific surface area of 450 m$^2$/g or more and an acid amount measured by an ammonia-TPD method of 0.38 mmol/g or more, said pentasil-type zeolite comprising secondary particles wherein said secondary particles have a diameter of aggregate of 0.3 to 50 μm.

2. The pentasil-type zeolite according to claim 1, wherein the pentasil-type zeolite comprises a pore volume being 0.60 mL/g or less.

3. The pentasil-type zeolite according to claim 1, wherein the pentasil-type zeolite comprises a molar ratio of silica to alumina being less than 150.

4. The pentasil-type zeolite according to claim 1, wherein the pentasil-type zeolite comprises, a molar ratio of tetra-coordinated aluminum to the sum of the tetra-coordinated aluminum and hexa-coordinated aluminum in a crystal being 90% or more.

5. The pentasil-type zeolite according to claim 1, wherein the pentasil-type zeolite comprises an alkali metal, with a molar ratio of the alkali metal to aluminum being 0.5 or less.

6. The pentasil-type zeolite according to claim 1, wherein primary particles randomly aggregate.

7. The pentasil-type zeolite according to claim 1, wherein the pentasil-type zeolite comprises phosphorus.

8. The pentasil-type zeolite according to claim 7, wherein the pentasil-type zeolite comprises a molar ratio of phosphorus to silicon and aluminum being 0.0005 or more.

9. The pentasil-type zeolite according to claim 1, wherein the acid amount measured by an ammonia-TPD method is 0.45 mmol/g or more.

10. A method for manufacturing the pentasil-type zeolite according to any one of claim 1, comprising crystallizing a mixture containing tetrabutylphosphonium cations, a silica source, an alumina source, an alkali metal source, and water, wherein a molar ratio of the alkali metal source to silica in the mixture is more than 0.04 and less than 0.10.

11. The manufacturing method according to claim 10, wherein a molar ratio of tetrabutylphosphonium cations to silica in the mixture is 0.04 or more and 0.3 or less.

12. The manufacturing method according to claim 10, wherein the mixture has the following molar composition:
SiO$_2$/Al$_2$O$_3$ of 40 or more and 200 or less,
TBP/SiO$_2$ of 0.04 or more and 0.3 or less,
SO$_4$/SiO$_2$ of 0 or more and 0.1 or less,
OH/SiO$_2$ of 0.05 or more and 0.5 or less,
H$_2$O/SiO$_2$ of 5 or more and 40 or less, and
M/SiO$_2$ of more than 0.04 and less than 0.1
(TBP represents tetrabutylphosphonium cations, and M represents the alkali metal).

13. A catalyst comprising the pentasil-type zeolite according to claim 1.

14. A method for manufacturing an aromatic hydrocarbon using a catalyst comprising the pentasil-type zeolite according to claim 1.

* * * * *